(12) United States Patent
Janzig et al.

(10) Patent No.: US 11,110,284 B2
(45) Date of Patent: Sep. 7, 2021

(54) MEDICAL DEVICE LEAD CONNECTION ASSEMBLY WITH GUIDE HUB

(71) Applicant: MEDTRONIC, INC., Minneapolis, MN (US)

(72) Inventors: Darren Janzig, Center City, MN (US); Robert J. Davies, Mounds View, MN (US); Seth M. Humphrys, Golden Valley, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 207 days.

(21) Appl. No.: 16/091,296

(22) PCT Filed: Apr. 13, 2017

(86) PCT No.: PCT/US2017/027347
§ 371 (c)(1),
(2) Date: Oct. 4, 2018

(87) PCT Pub. No.: WO2017/180831
PCT Pub. Date: Oct. 19, 2017

(65) Prior Publication Data
US 2019/0151664 A1    May 23, 2019

Related U.S. Application Data

(60) Provisional application No. 62/323,089, filed on Apr. 15, 2016.

(51) Int. Cl.
*A61N 1/375* (2006.01)
*A61N 1/05* (2006.01)
*A61N 1/39* (2006.01)

(52) U.S. Cl.
CPC ............. *A61N 1/3752* (2013.01); *A61N 1/05* (2013.01); *A61N 1/375* (2013.01); *A61N 1/3968* (2013.01)

(58) Field of Classification Search
CPC ........ A61N 1/05; A61N 1/375; A61N 1/3752; A61N 1/3968
See application file for complete search history.

(56) References Cited

U.S. PATENT DOCUMENTS 9,061,132 B1 *  6/2015  Zweber ............... A61N 1/37514
2002/0183818 A1 * 12/2002  Williams ............... A61N 1/056
607/122

(Continued)

OTHER PUBLICATIONS

International Search Report and Written Opinion for PCT/US2017/027347, filed Apr. 13, 2017; dated Jun. 26, 2017, 14 pages.

*Primary Examiner* — Jonathan T Kuo
*Assistant Examiner* — Vynn V Huh
(74) *Attorney, Agent, or Firm* — Mueting Raasch Group

(57) ABSTRACT

A medical device lead connection assembly includes an end connector element including a plurality of fixed connection element tabs extending from the end connector element to a tab distal end. A lead body includes a plurality of lead filars extending through the lead body and coupled to a corresponding fixed connection tab. A tubular guide hub extends from a hub proximal end to a hub distal end. The tubular guide hub includes a plurality of guide elements circumferentially disposed about an outer surface of the guide hub. The hub distal end is disposed within the lead body and the hub proximal end received within connection element tabs, and selected guide elements contact selected lead filars.

22 Claims, 2 Drawing Sheets

(56) References Cited

U.S. PATENT DOCUMENTS

| | | |
|---|---|---|
| 2003/0050680 A1 | 3/2003 | Gibson et al. |
| 2005/0222658 A1 | 10/2005 | Hoegh et al. |
| 2011/0165785 A1* | 7/2011 | Lindner ................ H01R 31/06 439/271 |
| 2012/0271381 A1* | 10/2012 | McIntyre ................ C22C 14/00 607/62 |
| 2015/0209575 A1 | 7/2015 | Black |

* cited by examiner

ND GUIDE HUB

MEDICAL DEVICE LEAD CONNECTION ASSEMBLY WITH GUIDE HUB

This application is the § 371 U.S. National Stage of International Application No. PCT/US2017/027347, filed Apr. 13, 2017, which claims the benefit of U.S. Provisional Application No. 62/323,089, filed Apr. 15, 2016, the disclosures of which are incorporated by reference herein in their entireties.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes present on a distal end portion of a lead. The proximal end portion of a lead, connected to a signal generator, typically contains a number of connectors corresponding to the number of electrodes. Conductors, also referred to as wire filars or filars, run within and along the lead body and electrically couple the connectors to the electrodes.

Fixing the filars that run within the lead body to an end connector is difficult. As the dimensions and size of the implantable medical devices decrease, fixing filars to an end connector becomes even more difficult. Aligning a number of very small filars and joining these filars to the correct connection point on an end connector requires a high level of skill and craftsmanship and takes time to join each filar to each end connector connection point.

SUMMARY

The present disclosure relates to a medical device lead connection assembly with a guide hub. The guide hub reliably and simply aligns lead filars onto an end connector connection tab.

In one illustrative embodiment, a medical device lead connection assembly includes an end connector element including a plurality of fixed connection element tabs extending from the end connector element to a tab distal end. A lead body includes a plurality of lead filars extending through the lead body and coupled to a corresponding fixed connection tab. A tubular guide hub extends from a hub proximal end to a hub distal end. The tubular guide hub includes a plurality of guide elements circumferentially disposed about an outer surface of the guide hub. The hub distal end is disposed within the lead body and the hub proximal end is received within the connector element, and selected guide elements contact selected lead filars.

In another illustrative embodiment, a medical device article includes a stimulator, a lead contact having at least one stimulation electrode, and a lead body providing stimulation signal communication to the stimulation electrode. The lead body includes an end connector assembly. The end connector assembly includes an end connector element having a plurality of fixed connection element tabs extending from the end connector element to a tab distal end. A plurality of lead filars extending through the lead body, each of the plurality of lead filars coupled to a corresponding fixed connection tab. A tubular guide hub extending from a hub proximal end to a hub distal end. The tubular guide hub includes a plurality of guide elements circumferentially disposed about an outer surface of the guide hub. The hub distal end is disposed within the lead body and the hub proximal end is received within the connector element, and selected guide elements contact selected lead filars.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
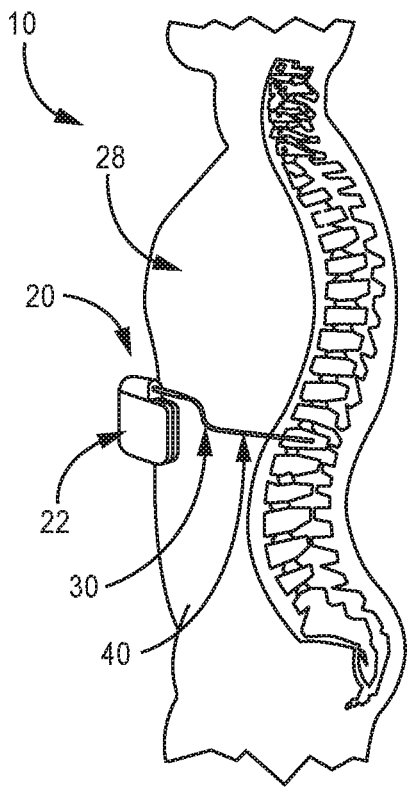
FIG. 1 is a diagrammatic representation of a general environmental view for a stimulation system embodiment.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The term "coupled" refers to two elements being attached to each other either directly (in direct contact with each other) or indirectly (having one or more elements between and attaching the two elements).

The present disclosure relates to a medical device lead connection assembly with a guide hub. The guide hub reliably and simply aligns lead filars onto end connector connection elements. The guide hub extends from a proximal end to a distal end where the distal end is disposed within the lead body and the proximal end is received within the connector element. Guide elements are circumferentially disposed about the guide hub to guide and provide filar management. An alignment feature may be disposed on the guide hub and be configured to mate with the end connector to provide rotational and axial alignment of the filars. The guide hub may provide filar management and filar alignment with the end connector connection tabs. The guide hub can reliably increase the coil pitch as compared to the coil pitch within the lead body. The coil pitch can be increased along the guide hub by at least 1.5 times or at least 2 times as compared to the coil pitch within the lead body. The lead filars can have a small diameter of less than 250 micrometers or less than 150 micrometers. The guide hub provides reliable filar placement and intimate filar contact with the end connector connection tabs and reliable weld joints even with filar trim length variation. While the present disclosure is not so limited, an appreciation of various aspects of the disclosure will be gained through a discussion of the examples provided below.

FIG. 1 shows a general environmental view 10 for an implantable stimulation system. While a stimulation system is illustrated, it is understood that any implantable medical device having a lead body may be utilized with the filar connection assembly described herein.

Stimulation system 20 includes a stimulator 22 (such as a neurostimulator, for example), an optional stimulation lead extension 30, and a stimulation lead 40. Stimulator 22 is typically implanted subcutaneously in a patient's body 28 at a location selected by the clinician; although FIG. 1 illustrates stimulator 22 implanted in the patient's abdomen, other locations are suitable. Stimulation lead 40 is typically fixed in place terminating near the desired location selected by the clinician using a device such as an adjustable anchor.

Figure 2:
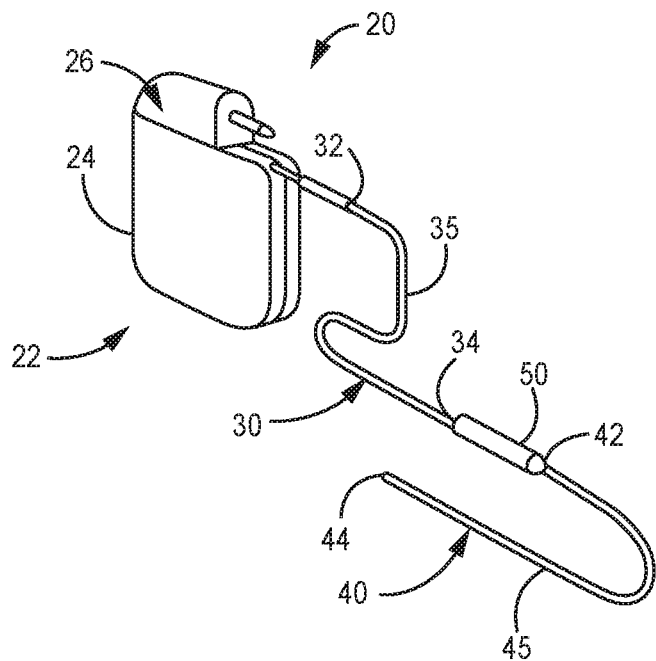
FIG. 2 is a perspective view of the illustrative neurostimulation system of FIG. 1.

FIG. 2 shows an enlarged view of implantable stimulation system 20 having implantable stimulator 22, stimulation lead 40, and optional lead extension 30. Implantable stimulator 22 has a housing 24, a power supply (for example, a battery) within housing 24, and stimulation electronics coupled to the power supply and coupled to a connector block 26, which is also known as a terminal block. Stimulation lead 40 has a lead proximal end 42, a lead distal end 44 and a lead body 45. At lead distal end 44 is an electrode contact having at least one stimulation electrode (not illustrated). Lead extension 30 has an extension proximal end 32, an extension distal end 34, and an extension body 35. Lead proximal end 42 connects to lead extension distal end 34 at connector 50; either or both lead proximal end 42 or extension distal end 34 may include an electrode tip that engages with connector 50.

Lead 40 and lead extension 30 provide electrical communication from stimulator 22 to the electrode contact at distal end 44. Lead distal end 44 contains at least one electrode but in most embodiments has a plurality of such electrodes (for example, 4, 8, 16, etc.). Extending through lead 40 and lead extension 30 are electrically conducting wires, often referred to as filars or wire filars, that couple stimulator 22 to the electrode contact and its electrode(s). The filars may form a multi-filar coil extending along the lead body length.

The lead filars may, for example, be stranded (made up of many small wires), braided-stranded or "BSW" (braided of many small wires), or solid or monofilament. Extending over and covering the wire filars is an electrically insulating jacket or sheath. Typically, this jacket is a polymeric material, such as ethylene tetrafluoroethylene (ETFE), polytetrafluoroethylene (PTFE), silicone rubber or polyurethane. Other materials that act as electrical insulators can be used. In some embodiments, a shielding layer or jacket may be present, optionally over the insulating jacket. An example of one suitable shielding layer is described in U.S. Patent Application Publication No. 2005/0222658.

This disclosure is directed to a filar connection assembly that includes a guide hub. The guide hub may provide filar management and filar alignment with the end connector connection tabs. This results in reliable intimate filar contact with the end connector connection tabs and reliable weld joints even with filar trim length variation and filars having a diameter of less than 200 micrometers. This connection assembly can be utilized in any number of filar connection points in the lead 40 and/or lead extension 30 to provide electrical communication from stimulator 22 to the electrode contact at distal end 44. It should be understood that the following discussion of the modular end pieces or interconnects of this invention makes reference to "lead", "leads", "lead body", and the like, generically, and that this discussion is not limiting to positions or uses of the end interconnects of this disclosure, but that they may be used at any location. It should also be understood that the end piece interconnector and the lead structures could be used with applications other than just stimulators.

Figure 3:
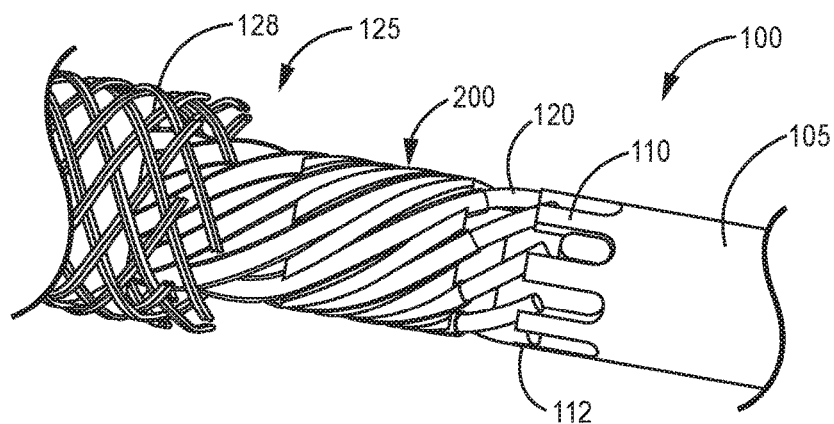
FIG. 3 is a cut-away side schematic view of an illustrative connection assembly with the guide hub.

FIG. 3 is a cut-away side schematic view of an illustrative connection assembly 100 with the guide hub 200. The medical device lead connection assembly 100 includes a plurality of lead filars 120 in contact with a corresponding plurality of connection tabs 110 at a connection point 112. The connection tab 110 forms a portion of the connection element 105 such as an end connector. The lead body 125 includes 4 or more, or 8 or more, or 10 or more or 12 or more filars 120 in helical or spiral wound along the lead body 125 forming a coil or multi-filar coil. Shielding 128 is illustrated partially covering the spiral wound filars 120. Once positioned as illustrated, lasers can heat and melt a portion of the lead filar 120 and/or the connection element 110 simultaneously to form the connection from the filar to the connection element 110.

In many embodiments, each of the contacting filars flex against a connection element so that one or both are in flexure, where one or both deflects within the elastic limit of each of the lead filars. The lead filars extend the length of the lead body and are in electrical connection with a lead contact at a distal end of the lead body, as described above. In some embodiments, the contacting forms an angle between the lead filars in a range from 1 to 70 degrees, or from 25 to 70 degrees, or from 30 to 50 degrees. The lead filars may have any useful size or diameter.

It has been found that the connection method is particularly useful when the lead filars 120 have a small diameter. In many of these embodiments the lead filar 120 has a diameter of less than 250 micrometers, or less than 200 micrometers, or less than 150 micrometers, or less than 125 micrometers, or less than 100 micrometers, or from 50 to 150 micrometers or from 50 to 125 micrometers or from 70 to 100 micrometers. The lead filar 120 may be insulated and this insulation may add an additional 5 to 40 micrometers of thickness about the insulated portion of the lead filar 120.

A weld joint is formed by heating and melting at least a portion of the end portion of each lead filar. The weld joint is initially held in the liquid state. Surface tension holds the liquid metal in the weld pool until it cools to the solid metal weld joint. The guide hub allows for a single presentation to the weld station and a simultaneous or sequential weld of all of the plurality of lead filars to the connection element tabs.

The melting step may form the weld without additional weld material. In many embodiments the weld is formed with a laser weld or an e-beam weld. This is particularly useful when the lead filars are formed of Titanium Molybdenum (TiMo) or a TiMo alloy. It has been found that β TiMo alloy increases in modulus and strength when heated to the liquid phase (by transforming a portion to an a crystal structure). After the melting step, the weld is cooled to complete the connection.

The guide hub 200 may form an angle between the lead filar 120 and a longitudinal axis of the lead body 125 in a range from 1 to 70 degrees or from 10 to 50 degrees or from 25 to 50 degrees. The guide hub 200 generally increases the pitch of the multi-filer coil as compared to the pitch of the multi-filar coil distal of the guide hub 200.

The filars 120 in helical or spiral wound along the lead 125 body may form a multi-filar coil having an outer diameter of less than 1.5 millimeters or less than 1 millimeter or in a range from 500 to 900 micrometers, or in a range from 625 to 875 micrometers. This multi-filar coil may have an inner diameter in a range from 200 to 1000 micrometers, or from 350 to 800 micrometers, or from 250 to 600 micrometers. The multi-filar coil inner diameter may define an open lumen that may be configured to receive a stylet for lead placement.

Figure 4:
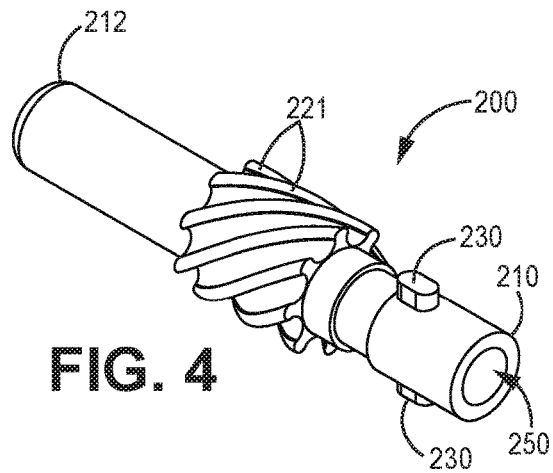
FIG. 4 is a perspective diagram view of an illustrative guide hub.
Figure 5:
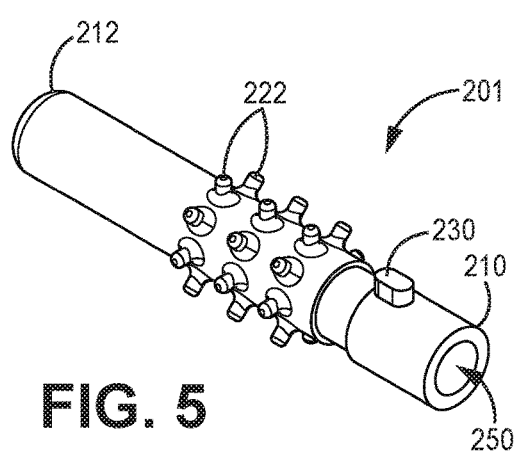
FIG. 5 is a perspective diagram view of another illustrative guide hub.

FIG. 4 is a perspective diagram view of an illustrative guide hub 200. FIG. 5 is a perspective diagram view of another illustrative guide hub 201. The guide hub 200, 201 extends from a proximal end 210 to a distal end 212 where the distal end 212 is disposed within the lead body (see FIG. 3, 125) and the proximal end 210 is received within the connection tabs (see FIG. 3, 110) of the end connector (see FIG. 3, 105). A lumen 250 may extend through the hub 200, 201 extends from a proximal end 210 to a distal end 212 to allow a stylet, for example to pass through.

Guide elements 221, 222 are circumferentially disposed about the guide hub 200, 201 to guide and provide filar management. In many embodiments the guide elements 221 are a plurality of co-extending spiral channels 221. The lead filar 120 is disposed within the spiral channel 221.

In other embodiments, the guide elements 222 are a plurality of posts 222 extending away from the outer surface of the tubular guide element 201. The lead filar 120 is disposed between the plurality of posts 222. The posts 222 may be arranged along a longitudinal axis along a length of the tubular guide hub 201. The posts 222 may be arranged along a lateral axis along a length of the tubular guide hub 201. In many embodiments there are at least 8 or at least 10 or at least 12 posts 222.

An alignment feature 230 may be disposed on the guide hub 200, 201 and be configured to mate with the end connector (105) to provide rotational and axial alignment of the filars (120). The guide hub 200, 201 may provide filar management and filar alignment with the end connector connection tabs (110). In some embodiments the guide hub 200, 201 includes two alignment features 230.

In many embodiments, the alignment element 230 is a protrusion extending from the tubular guide hub 200, 201 and is located between the proximal end 210 and the plurality of guide elements 221, 222. The alignment element 230 may be received between adjacent connection element tabs (110) as illustrated in FIG. 3.

The guide hub 200, 201 may assist in varying the coil pitch of the lead filars 120. The guide hub 200, 201 may assist in increasing the coil pitch of the lead filars 120. Varying the coil pitch of a multi-filar coil 120 is difficult, especially with small diameter lead filars 120 as described herein. It is preferred that the lead filars 120 have a small or tight coil pitch within the lead body to provide structural support to the lead body. However, this tight coil pitch is difficult to terminate to an end connector element. Increasing the lead filar 120 coil pitch assists in termination to an end connector element. The guide hub 200, 201 may assist in increasing the coil pitch of the lead filars 120, as illustrated in FIG. 3.

The lead filars may form a greater coil pitch along the plurality of guide elements than within the lead body. In many embodiments, the coil pitch along the guide elements is at least 1.5 times greater or at least 2 times greater than the coil pitch within the lead body.

The guide hub 200, 201 may have an outer diameter of less than 1 millimeter or in a range from 500 to 900 micrometers or in a range from 625 to 875 micrometers. This multi-filar coil may have an inner diameter in a range from 100 to 700 micrometers or from 250 to 550 micrometers. The guide hub 200, 201 inner diameter may define an open lumen that may be configured to receive a stylet for lead placement.

Thus, embodiments of the MEDICAL DEVICE LEAD CONNECTION ASSEMBLY WITH GUIDE HUB are disclosed. All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A medical device lead connection assembly comprising: an end connector element comprising a connector element body and a plurality of fixed connection element tabs, each of the plurality of fixed connection element tabs extending from the connector element body to a tab distal end; a lead body comprising a plurality of lead filars extending through the lead body, each of the plurality of lead filars is coupled to a corresponding fixed connection element tab of the plurality of fixed connection element tabs; a tubular guide hub extending from a hub proximal end to a hub distal end, the tubular guide hub comprising a plurality of guide elements circumferentially disposed about an outer surface of the guide hub and spaced apart from the hub proximal end, the hub distal end disposed within the lead body and the circumference of the hub proximal end received within the end connector element, and selected guide elements of the plurality of guide elements contact selected lead filars of the plurality of lead filars.

2. The assembly according to claim 1, wherein the end connector element comprises at least 8 fixed connection element tabs.

3. The assembly according to claim 1, wherein the plurality of lead filars forms a helical structure extending through the lead body and along the tubular guide hub.

4. The assembly according to claim 1, wherein the tubular guide hub comprises an alignment element arranged and configured to mate with the end connector element and align the plurality of filars with the plurality of fixed connection element tabs.

5. The assembly according to claim 4, wherein the alignment element is a protrusion extending from the tubular guide hub and is located between the hub proximal end and the plurality of guide elements.

6. The assembly according to claim 4, wherein the alignment element is received between adjacent connection element tabs of the plurality of fixed connection element tabs.

7. The assembly according to claim 1, wherein the plurality of guide elements comprises a plurality of co-extending spiral channels and a selected lead filar of the plurality of lead filars is disposed within a selected spiral channel of the plurality of co-extending spiral channels.

8. The assembly according to claim 1, wherein the plurality of guide elements comprises a plurality of posts extending away from the outer surface of the tubular guide hub and the plurality of lead filars is disposed between the plurality of posts.

9. The assembly according to claim 8, wherein selected posts are arranged along a longitudinal axis along a length of the tubular guide hub.

10. The assembly according to claim 8, wherein selected posts are arranged along a lateral axis along a length of the tubular guide hub.

11. The assembly according to claim 1, wherein each of the lead filars form a greater coil pitch along the plurality of guide elements than within the lead body.

12. The assembly according to claim 11, wherein the coil pitch along the guide elements is at least 1.5 times greater than the coil pitch within the lead body.

13. The assembly according to claim 1, wherein each of the lead filars have a diameter of less than 250 micrometers.

14. The assembly according to claim 1, wherein each of the lead filars are formed of Titanium Molybdenum (TiMo) or a TiMo alloy.

15. A medical device article comprising: a stimulator; a lead contact comprising at least one stimulation electrode; a lead body providing stimulation signal communication to the stimulation electrode, the lead body comprising an end connector assembly, the end connector assembly comprising: an end connector element comprising a connector element body and a plurality of fixed connection element tabs, each of the plurality of fixed connection element tabs extending from the connector element body to a tab distal end; a plurality of lead filars extending through the lead body, each of the plurality of lead filars is coupled to a corresponding fixed connection element tab of the plurality of fixed connection element tabs; a tubular guide hub extending from a hub proximal end to a hub distal end, the tubular guide hub comprising a plurality of guide elements circumferentially disposed about an outer surface of the guide hub and spaced apart from the hub proximal end, the hub distal end disposed within the lead body and the circumference of the hub proximal end received within the end connector element, and selected guide elements of the plurality of guide elements contact selected lead filars of the plurality of lead filars.

16. The article according to claim 15, wherein the end connector element comprises at least 8 fixed connection element tabs and an equal number of lead filars extend through the lead body.

17. The article according to claim 15, wherein the guide hub comprises an alignment element arranged and configured to mate with the end connector element and align the plurality of filars with the plurality of fixed connection element tabs.

18. The article according to claim 17, wherein the alignment element is a protrusion extending from the tubular guide hub and is located between the hub proximal end and the plurality of guide elements.

19. The article according to claim 17, wherein the alignment element is received between adjacent connection element tabs of the plurality of fixed connection element tabs.

20. The article according to claim 15, wherein each of the lead filars form a greater coil pitch along the plurality of guide elements than within the lead body.

21. The article according to claim 20, wherein the coil pitch along the guide elements is at least 1.5 times greater than the coil pitch within the lead body.

22. The article according to claim 15, wherein each of the lead filars have a diameter of less than 250 micrometers.

* * * * *